US009255002B2

(12) United States Patent
Luo et al.

(10) Patent No.: US 9,255,002 B2
(45) Date of Patent: Feb. 9, 2016

(54) APPARATUS AND METHOD FOR FORMING SELF-ASSEMBLY ARRAYS

(75) Inventors: Dan Luo, Ithaca, NY (US); Wenlong Cheng, Wantirna South (AU)

(73) Assignee: Cornell University, Ithaca, NY (US)

( * ) Notice: Subject to any disclaimer, the term of this patent is extended or adjusted under 35 U.S.C. 154(b) by 830 days.

(21) Appl. No.: 12/888,146

(22) Filed: Sep. 22, 2010

(65) Prior Publication Data

US 2011/0177978 A1 Jul. 21, 2011

Related U.S. Application Data

(60) Provisional application No. 61/244,765, filed on Sep. 22, 2009.

(51) Int. Cl.
*B82Y 40/00* (2011.01)
*B82Y 30/00* (2011.01)
*B81C 99/00* (2010.01)
*G03F 7/004* (2006.01)

(52) U.S. Cl.
CPC ............. *B82Y 40/00* (2013.01); *B81C 99/0025* (2013.01); *B82Y 30/00* (2013.01); *B81C 2201/0149* (2013.01); *B81C 2201/0187* (2013.01)

(58) Field of Classification Search
CPC ............ Y10S 977/773; Y10S 977/774; C12Q 2563/155
See application file for complete search history.

(56) References Cited

PUBLICATIONS

Cheng et al. (Nature Nanotechnology, 2008, 3:682-690).*
Ko et al. (Nano Letters, 2007, 7(7):1869-1877).*
Pan et al. (Applied Physics Letters, 2008, 93:234104).*
Kim et al. (J. Amer. Chem. Soc., 1996, 118:5722-5731).*
Liu et al. (Phys. Chem. Chem. Phys., 2002, 4, 6059-6062).*

\* cited by examiner

*Primary Examiner* — Jeremy C Flinders
(74) *Attorney, Agent, or Firm* — Miller, Matthias & Hull LLP

(57) ABSTRACT

Apparatus and methods for forming self-assembly arrays of substances, such as nanoparticles, on a substrate are disclosed. The apparatus may include a substrate supporting a liquid composition including the substance and a solvent, and a removable micro-mold placed over the substrate and the liquid composition. To form the self assembly arrays of the substance, the solvent may be evaporated through at least one evaporation channel formed between the micro-mold and the substrate. The evaporation channel may be adjustable by subjecting the micro-mold to a positive pressure.

19 Claims, 19 Drawing Sheets

Edge dewetting at pressure 4.9 N/ cm²

Edge 3D supra crystal

APPARATUS AND METHOD FOR FORMING SELF-ASSEMBLY ARRAYS

CROSS-REFERENCE TO RELATED APPLICATION

This application is based on and claims priority from U.S. provisional Application Ser. No. 61/244,765, filed on Sep. 22, 2009.

BACKGROUND OF THE DISCLOSURE

1. Technical Field

This disclosure generally relates to methods and apparatus for forming self-assembly arrays of substances, such as nanoparticles, on a substrate. In particular, this disclosure relates to the use of a micro-mold to control the dewetting dynamics of a liquid composition containing the substances and a solvent.

2. Description of the Related Art

Development of nanotechnology focusing on the control of matter on an atomic and molecular scale has gained significant interest in recent decades. In general, nanotechnology deals with structures having sizes of 100 nanometers or smaller, and involves developing materials or devices within that size. Nanotechnology is very diverse, ranging from novel extensions of conventional device physics, to completely new approaches based upon molecular self-assembly, to developing new materials with dimensions on a nanoscale.

Molecular self-assembly is an important aspect of bottom-up approaches to nanotechnology. Using molecular self-assembly the final (desired) structure is programmed in the shape and functional groups of the molecules. Self-assembly is referred to as a 'bottom-up' manufacturing technique in contrast to a 'top-down' technique such as lithography where the desired final structure is carved from a larger block of matter. In the speculative vision of molecular nanotechnology, microchips of the future might be made by molecular self-assembly.

Transition metal nanoparticles, such as gold nanoparticles, have been the focus of intense interest recently due to their potential use in the fields of optics, immunodiagnostics, and electronics. The transition metal nanoparticles may exist in a variety of shapes including spheres, rods, cubes, and caps. In application, the transition metal nanoparticles are generally coordinated to, and stabilized by, a ligand.

The development of parallel, inexpensive approaches to patterning crystalline materials is essential in making use of their outstanding properties in bottom-up nanodevices. Nanoparticle superlattices comprise a new class of crystals ('supra-crystal') with collective properties that are different from those of bulk phase materials, isolated nanoparticles and even disordered nanoparticle assemblies. For instance, coherent vibrational modes can only appear in highly ordered nanoparticle superlattices, and synergistic effects in superlattices can lead to enhanced p-type conductivity. Hence, nanoparticle superlattices are poised to become a 'new periodic table', which could be used for high performance devices such as high-density data storage, more efficient energy harvesting systems and ultra-sensitive biosensors.

Applying the collective properties of nanoparticle superlattice entities in nanodevices usually requires methods capable of patterning them into desired structures while maintaining a high degree of internal order. However, superlattices usually form from the evaporation of a drop of nanoparticle solution, which is essentially a far-from-equilibrium process. Capillary flow induced by a non-uniform evaporation field and fluid fluctuations during late-stage drying often lead to irregular features such as isolated islands, worm-like domains, ring-like structures and cellular networks. Owing to the statistical nature of drying-mediated self-assembly, it remains a challenge to pattern superlattices with comprehensive control over internal order and overall morphologies.

SUMMARY OF THE DISCLOSURE

Apparatus and methods for forming self-assembly arrays of substances, such as nanoparticles, on a substrate are disclosed. In one non-limiting embodiment, the apparatus may include a substrate supporting a liquid composition including the substance and a solvent, and a removable micro-mold placed over the substrate and the liquid composition. To form the self assembly arrays of the substance, the solvent may be evaporated through at least one evaporation channel formed between the micro-mold and the substrate. The evaporation channel may be adjustable by subjecting the micro-mold to a positive pressure.

In another non-limiting embodiment, an apparatus for bridging microelectrodes is disclosed. The apparatus may include a substrate having at least two microelectrodes and supporting a liquid composition including the nanoparticles and a solvent, and a removable micro-mold placed over the substrate and the liquid composition and bridging the at least two microelectrodes. The solvent may be evaporated through at least one evaporation channel formed between the micro-mold and the substrate.

In another non-limiting embodiment, the method may include the steps of depositing on the substrate a liquid composition including the substance and a solvent, placing a removable micro-mold over the substrate and the liquid composition, and allowing the solvent to be evaporated through at least one evaporation channel formed between the micro-mold and the substrate. The method may further include the steps of applying positive pressure to the micro-mold when the solvent is evaporated through the evaporation channel, and removing the micro-mold from the substrate after the solvent is evaporated.

The localization and pattern of the self-assembly arrays formed on the substrate may be controlled by the shape and dimension of the micro-mold, the dewetting dynamics of the liquid composition containing the substances and solvent, or a combination of both. For example, self-assembly arrays of the substance may be formed toward the micro-mold (i.e. edge-dewetting) when the micro-mold is subjected to a first (or lower) positive pressure when the solvent is evaporated through the evaporation channel. On the other hand, the self-assembly arrays of the substance may be formed away from the micro-mold (i.e. center dewetting) when the micro-mold is subjected to a second (or higher) positive pressure when the solvent is evaporated through the evaporation channel. As used in the present disclosure, the term "toward" or "away from" the micro-mold refer to directions related to the sidewall of the micro-mold.

The micro-mold may be made of polydimethylsiloxane or other suitable materials and the substrate may be silicon or micro-patterned electrodes. The substance to be formed as self-assembly arrays may be nanoparticles, quantum dots, conductive polymers, or crystalline salts. In one embodiment, the nanoparticles used in this disclosure each include a center core and spacer ligands attached to the center core. The center core may be a transition metal and the spacer ligands may be alkyl groups or nucleic acids.

Other advantages and features of the disclosed methods and device will be described in greater detail below. It will also be noted here and elsewhere that the device or method disclosed herein may be suitably modified to be used in a wide variety of application by one of ordinary skill in the art without undue experimentation.

BRIEF DESCRIPTION OF THE DRAWINGS

For a more complete understanding of the disclosed device and methods, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed device or method which render other details difficult to perceive may have been omitted. It should be understood, of course, that this disclosure is not limited to the particular embodiments illustrated herein.

DETAILED DESCRIPTION OF THE DISCLOSURE

Figure 1A:
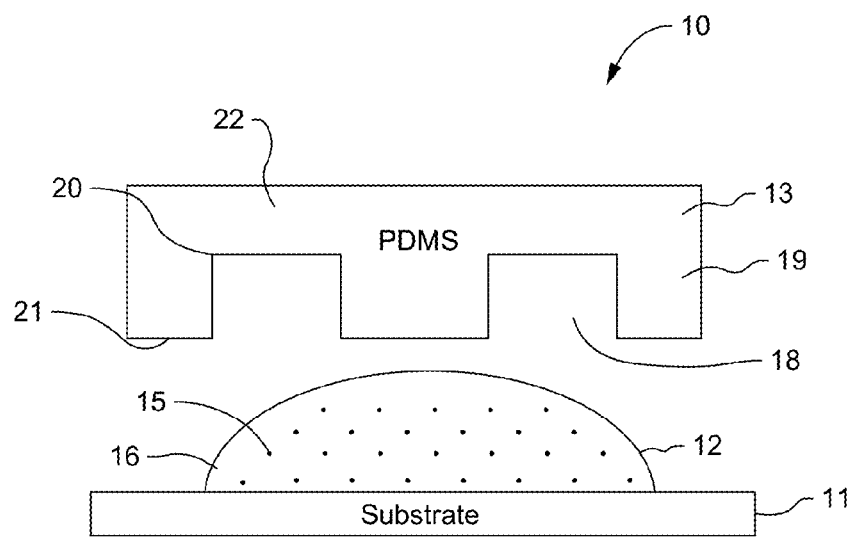
FIG. 1a is a schematic illustration of an apparatus according to one aspect of this disclosure.
Figure 1B:
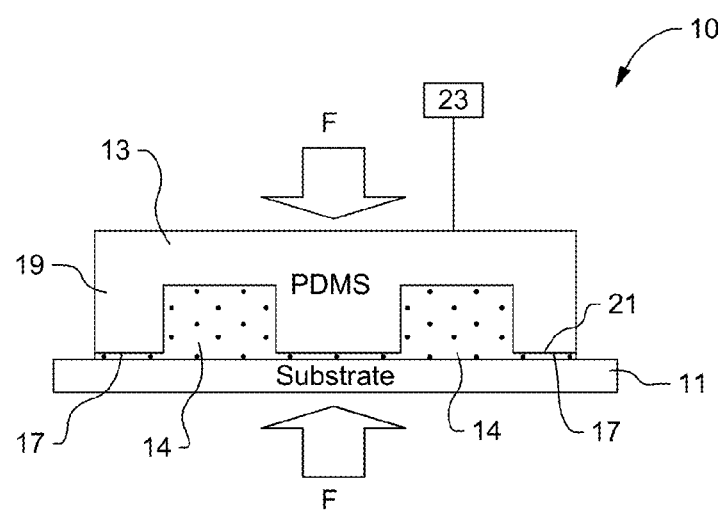
FIG. 1b is a schematic illustration of the apparatus in FIG. 1a, with the micro-mold placed over the substrate and liquid composition to form the evaporation channel.

This disclosure generally relates to methods and apparatus for forming self-assembly arrays of substances, such as nanoparticles, on a substrate. Referring now to FIGS. 1a-b, a non-limiting embodiment of the disclosed apparatus 10 is illustrated as including a substrate 11 supporting a liquid composition 12, and a removable micro-mold 13 placed over the substrate 11 and liquid composition 12 to mold the liquid composition into microdroplets 14. The liquid composition generally includes the substance 15 and a solvent 16. The micro-mold 13 and substrate 11 defines at least one evaporation channel 17, through which the solvent 16 of the liquid composition 12 can be evaporated from the surface of the substrate 11, leaving the substance 15 deposited on the substrate 11, a process referred to throughout this disclosure as "dewetting." Without wishing to be limited by any particular theory, it is contemplated that the dewetting dynamics of the liquid composition and/or the localization of the substance deposited on the substrate may be regulated by manipulating the substrate 11, the liquid composition 12, and/or the micro-mold 13, an insight heretofore unknown.

The substrate 11 may be suitable solid material upon which the substance 15 may be deposited. In some embodiments, affinity between the substance 15 and substrate 11 may allow the substance 15 to adhere to the substrate 11 after evaporation of the solvent 16 without the need of any binders, adhesives, or other intermediary materials positioned between the substance 15 and substrate 11. The substrate 11 may have a planar or curved surface upon which the substance 15 is deposited. In one embodiment, the substrate 11 is made of silicon. In another embodiment, the substrate 11 comprises one or more microelectrodes.

The micro-mold 13 may be made of polydimethylsiloxane (PDMS) or other suitable materials that can patterned with micro- or even nano-sized features. It is to be understood that the term "micro" in the micro-mold of this disclosure is meant to refer to the miniature size of the mold features and should be interpreted as encompassing micro-molds with either micro- or nano-sized features. The features of the micro-mold 13 may have a wide variety of shapes, dimensions, and spacing. For example, the features may be circular, oval, triangular, square, rectangular, polygonal, or of other regular or irregular shapes suitable for forming desirable patterns of the substance on the substrate. The micro-mold 13 may be uniplexed, in which the features are uniform and so are the patterns formed on the substrate. The micro-mold 13 may also be multiplexed, in which the features are non-uniform and the substances are deposited on the substrate with different shapes and patterns on different locations of the substrate. The features may be formed through a wide variety of known techniques. In one non-limiting embodiment, a pre-defined array of micro- or nano-sized openings is created photolithographically in a photoresist mask, and is then transferred into a PDSM micro-mold through an etching process.

The substance 15 to be deposited and/or patterned on the substrate 11 as self-assembly arrays may include nanoparticles, quantum dots, conductive polymers, crystalline salts. In one embodiment, the nanoparticles used in this disclosure each include a center core and spacer ligands attached to the center core. Suitable materials for the center core may include, but are certainly not limited to, transition metals such as gold, silver, platinum, cadmium, etc. In one embodiment, the nanoparticles are gold nanoparticles.

In order to facilitate the organization of the nanoparticles on the substrate during the dewetting process, each of the nanoparticles may be coordinated with a plurality of nucleic acids, such as those in the form of DNAs, RNAs, PNAs, LNAs, GNAs, TNAs, and mixtures thereof. In one embodiment, the nucleic acids are DNAs selected from a group consisting of single stranded DNAs, double stranded DNAs, hairpin DNAs, dendrimer DNAs, quadruplex DNAs, and mixtures thereof. The average number of nucleic acids coordinated with each nanoparticle may be at least 100. In one embodiment, each nanoparticle according to this disclosure is coordinate with from 200 to 300 nucleic acids. When supported by the substrate, the nucleic acids coordinated with the nanoparticles may be substantially free of Watson-Crick base-pairing.

Although other spacer ligands, such as alkylthiols may also be used in light of this disclosure, one feature of using nucleic acids as the spacer ligand is that it may allow the interparticle-distance of the nanoparticles to be fine-tuned by varying the length of the nucleic acids, thereby further contributing to the versatility and precision of the methods disclosed herein, a synergistic benefit heretofore unknown. In one embodiment, the interparticle-distance is from about 2 nm to about 25 nm. In yet another embodiment, the interparticle-distance is from about 3 to about 25 nm. The length of the nucleic acids may be from about 5 to about 90 nucleotide units, such as dT.

For example, self assembly high-quality nanoparticle superlattices may be formed on a silicon substrate by the disclosed method. These superlattices formed from single-stranded DNA-capped gold nanoparticles in a drying-mediated self-assembly process. DNA was used here as a spacer ligand similar to alkyl ligands, unlike DNA programmable self-assembly in buffer solutions. DNA packing density and length are dominant factors determining the formation of high-quality superlattices and interparticle spacing.

One feature of the DNA-capped nanoparticles is that they may have a relatively high solubility in water (free of aggregation at an unusually high concentration of 83 mg/ml), which enables patterning of 3D superlattices. Another feature is that the superlattices in this disclosure may be in the size range of interesting surface plasmon resonance properties and can be readily imaged by scanning electron microscopy (SEM). By controlling local crystallization events of these DNA-capped nanoparticles, well-organized superlattices may be readily patterned into versatile features while parameters affecting the patterning process, such as molding pressures, micro-mold specifications and particle concentrations, may be investigated.

Other suitable substances 15 for use in this disclosure may include quantum dots such as CdSe/ZnS, conductive polymers such as poly(3,4-ethylenedioxythiophene)-poly(styrenesulfonate), and crystalline salts, such as sodium chloride. It is to be understood that this disclosure is not limited to the substances enumerated herein and a wide variety of substances may be used in light of this disclosure without undue experimentation.

To deposit or pattern organized self assembly arrays of the substance 15 on the substrate 11, the liquid composition 12 may be in the form a solution, dispersion, colloid, or suspension. When nucleic acid coordinated transition metal nanoparticles are used, the enhanced stability of the nanoparticles allows formulation of the liquid composition 12 in a wide range of concentrations (e.g. up to about 83 mg/ml). The solvent 16 may be water, organic solvents, and mixtures thereof. When nucleic acid coordinated transition metal nanoparticles is used, the solvent 16 may have properties that disfavors Watson-Crick base-pairing. For example, the liquid carrier may be a low-salt buffer (<1 mM NaCl). Suitable organic solvents may include short chain alcohols and other solvent that may be evaporated through the evaporation channel at a rate suitable for the formation of the self assembly arrays on the substrate. The array of substance 15 deposited or patterned on the substrate 11 formed through the disclosed methods and apparatus may be 1D linear structures, 2D superlattices, or 3D supra-crystals high orders of organization.

As illustrated in FIG. 1a, the micro-mold 13 may include one or more cells 18 each defined by a continuous sidewall 19 extending between top and bottom edges (20, 21). The cell 18 may also include an optional top wall 22 that seals against the top edge 20 so as to prevent evaporation of the solvent 16 from the top of the cell 18. In some non-limiting embodiments, the depth of the cells 18 may be from about 2 μm to about 20 μm and the side length or diameter of the cells 18 may be from about 2 μm to about 20 μm. When the micro-mold 13 is placed over the substrate 11 and liquid composition 12 as illustrated in FIG. 1b, the liquid composition 12 is molded into one or more microdroplets 14 that are contained within, and engaging the sidewall of, the cell 18. The evaporation channel 17, in this embodiment, is defined between the bottom edge 21 and the substrate 11, and can be adjusted by applying and manipulating positive pressure on the micro-mold 13. For example, when the micro-mold 13 is subjected to no or relatively low positive pressures, a wide evaporation channel 17 is formed between the micro-mold 13 and substrate 11, allowing the solvent 16 to be evaporated at a faster rate. Conversely, when the micro-mold 13 is subjected to relatively high positive pressures, a narrow evaporation channel 17 is formed between the micro-mold 13 and substrate 11, resulting in slower evaporation of the solvent 16 from the substrate 11. To that end, the apparatus 10 may further include an optional pressurizer 23 operatively connected to the micro-mold 13, the substrate 11, or both. In a non-limiting embodiment, the pressurizer 23 may be a weight resting directly on the top of the micro-mold. Other pressurizers of hydraulic, pneumatic, and electric nature may also be used. When there is direct contact between the pressurizer 23 and the top of the micro-mold 13, the optional top wall 22 may be replaced by the bottom contact surface of the pressurizer 23.

Moreover, unlike natural liquid droplets, which usually have quasi-spherical cap shapes, molded microdroplets 14 in this disclosure may have well-defined shapes, volumes, locations and contact line boundaries. Under different pressures, these 'artificial' microdroplets 14 may display distinct, highly controllable dewetting dynamics. For example, when the micro-mold 13 is under high pressure, a single microdroplet 14 may form on the substrate in the middle of the micro-mold 13, a process hereinafter referred to as "center dewetting" in this disclosure. On the other hand, under lower pressures the microdroplet 14 may collapse in the middle of the micro-mold, forming a 'microdroplet-corral' that remains attached to the sidewall 19 and bottom edge 21 of the micro-mold 13 for a period of time, a process hereinafter referred to as "edge dewetting."

Figure 2A:
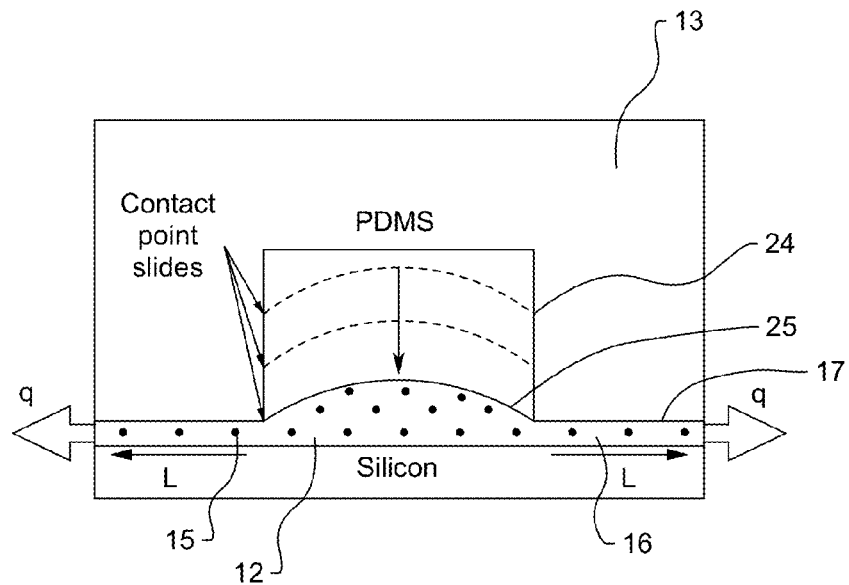
FIG. 2a is an enlarged partial view of the apparatus in FIG. 1b, showing a center-dewetting embodiment of the apparatus.
Figure 2B:
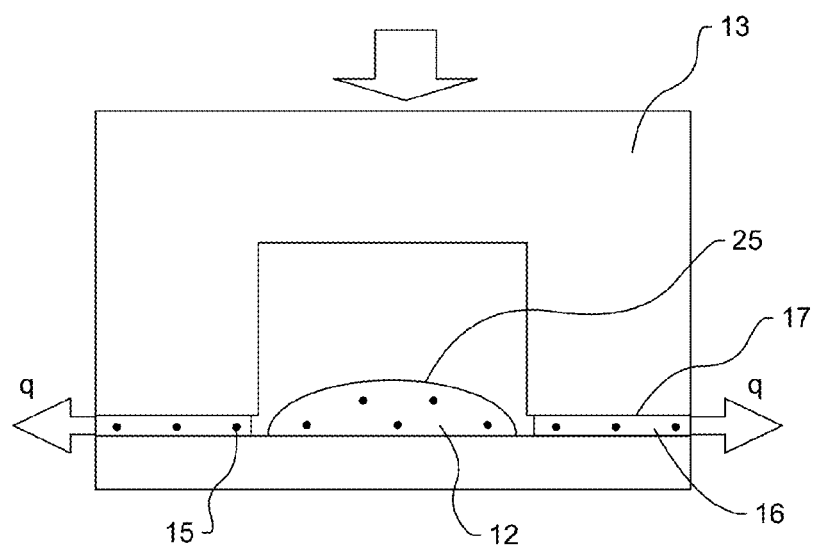
FIG. 2b is a schematic illustration of the apparatus in FIG. 2a, showing the liquid composition breaking off the micro-mold sidewall.
Figure 3A:
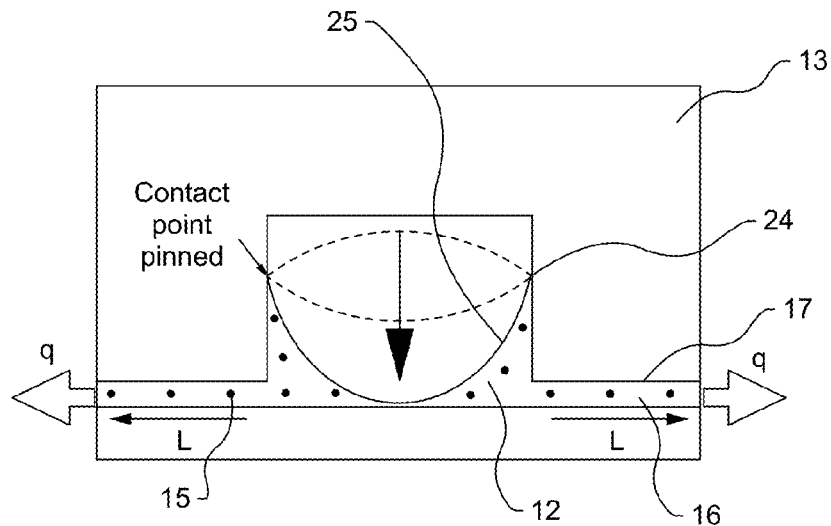
FIG. 3a is an enlarged partial view of the apparatus in FIG. 1b, showing an edge-dewetting embodiment of the apparatus.
Figure 3B:
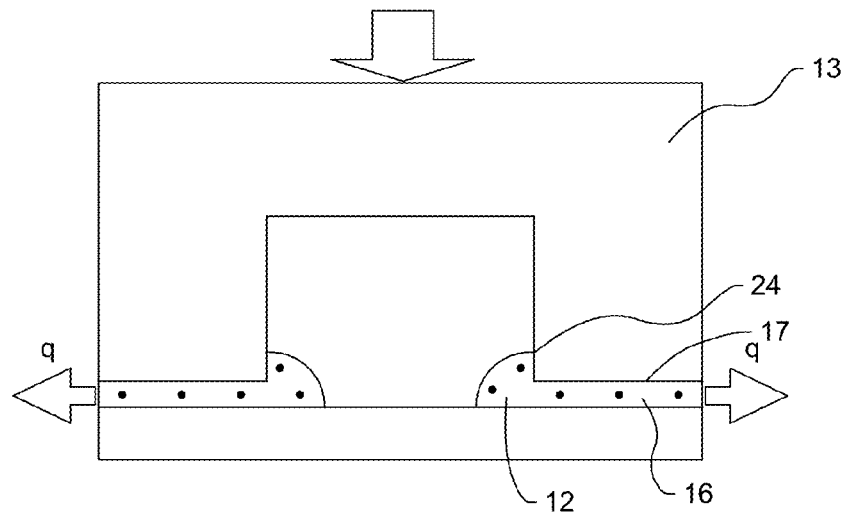
FIG. 3b is a schematic illustration of the apparatus in FIG. 3a, showing the liquid composition adhering to the micro-mold sidewall while breaking in the middle.

As illustrated in FIG. 2a, which illustrates a center dewetting process, the solvent 16 is slowly evaporated out of the evaporation channel 17, inducing a slow deformation of the meniscus. Under these conditions, internal currents within the liquid composition 12 may be sufficient to keep the liquid composition 12 near the contact point 24 dilute and allow it to slip down the sidewall 19 of the micro-mold 13. Eventually, the contact point 24 approaches the underlying substrate under the mold and breaks free of the bottom edge 21 as the microdroplet 14 recedes away from the micro-mold 13, as illustrated in FIG. 2b. Conversely, during edge dewetting as illustrated in FIG. 3a, the meniscus 25 deforms rapidly, concentrating the substance 15 at the bottom edge 21 of the micro-mold 13, which further expedites evaporation of the solvent 16 through the evaporation channel 17 near the bottom edges 21, thereby allowing the contact point 24 to remain pinned to the sidewall 19 of the micro-mold 13. Turning to FIG. 3b, the meniscus 25 eventually ruptures in the center when it approaches the substrate 11 and further recedes toward the bottom edge 21 of the micro-mold 24.

Although the three dimensional (3D) details of those dewetting processes are still not completely clear, it is found that high concentrations of the substance at the air-solution—solid interface strengthen the forces pinning the contact point 24 to the sidewall 19. In other words, when the meniscus 25 near the contact point deforms in a way that concentrates solutes near this point, the contact point 24 may remain pinned. Conversely, if the meniscus 25 deforms in a way that keeps the area near the contact point diluted, the contact point 24 will tend to slip down the sidewall 19.

Without wishing to be bound by any particular theory, it is hypothesized that one possible explanation for the solvent 16 leaving the micro-mold 13 at a slower rate under high pressure (center dewetting) than under low pressure (edge dewetting) is the Poiseuille's law for flow between parallel plates:

$$q = \frac{\Delta P h^4}{12\mu L}$$

where $\Delta P$ is the pressure gradient between the substrate 11 and the bottom edge 21 of the micro-mold 13, q is the flow out of the micro-mold 13, h is the height of the evaporation channel 17, $\mu$ is the dynamic viscosity of the liquid composition 12, and L is the length of the evaporation channel 17. As the micro-mold 13 "floats" on the solute, $\Delta P$ and h are inversely related. Thus, increased pressure may decrease the gap height and may have a large effect on retarding q, which may explain why center dewetting is slower than edge dewetting. Although only full contact point slip and full contact point pin are illustrated in FIGS. 2a-b and 3a-b, a variety of intermediate pin-slip behaviors may occur as hybrids of those two conditions. In addition, the micro-mold 24 may deform under pressure, which may also influence meniscus shapes and contact points, leading to more complicated pin-slip motions. Hence, control over the dewetting dynamics of molded microdroplets makes it possible to pattern a variety of materials through regulating local drying-mediated deposition of the substance 15 on the substrate 11.

Figure 4A:
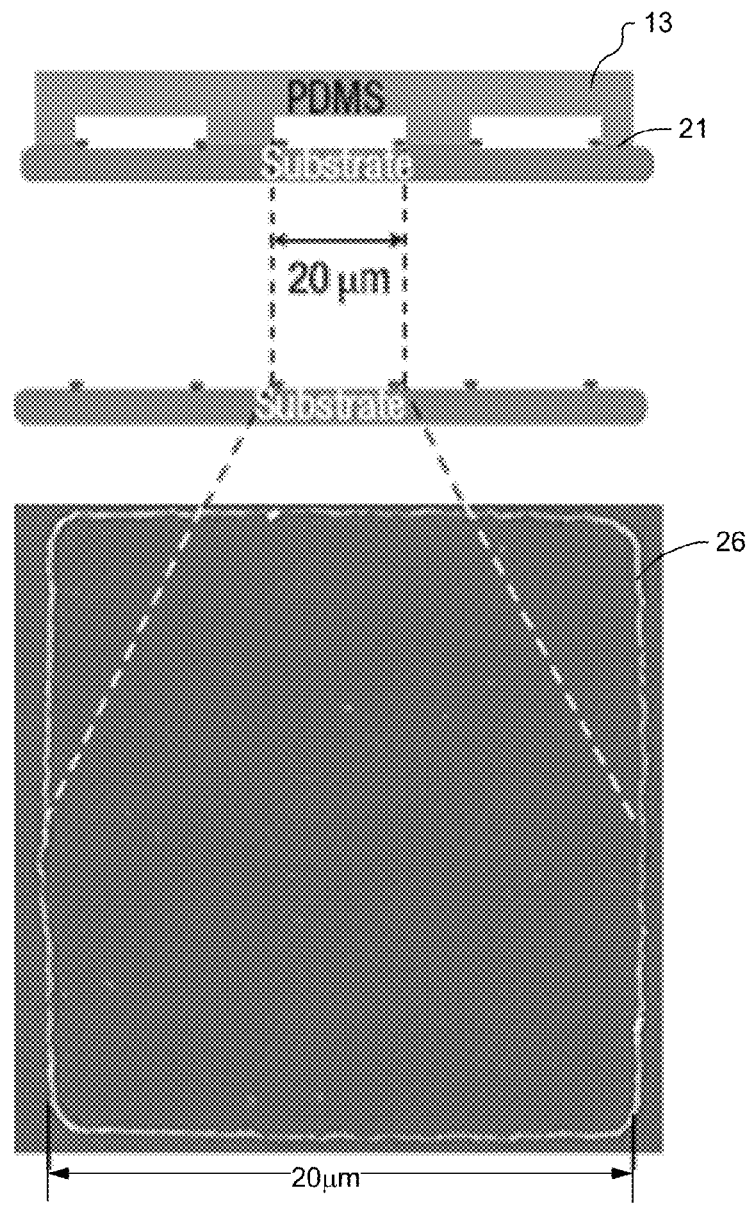
FIG. 4a illustrates an edge-defined corral formed through an edge-dewetting process (low pressure: 0.1 N/cm$^2$; cell dimension: 20 μm×20 μm sides; 8.5 μm depth)

Turning now to FIG. 4a, under a low molding pressure and edge-dewetting condition, nucleation and growth of superlattices are generally confined to the bottom edge 21 of the micro-mold 13, resulting in edge-defined corrals 26. These corrals 26 remained intact on the silicon surface after peeling off the micro-mold 13 because of the strong adhesion between the nanoparticles 15 and the high-surface-energy silicon substrate 11.

Figure 4B:
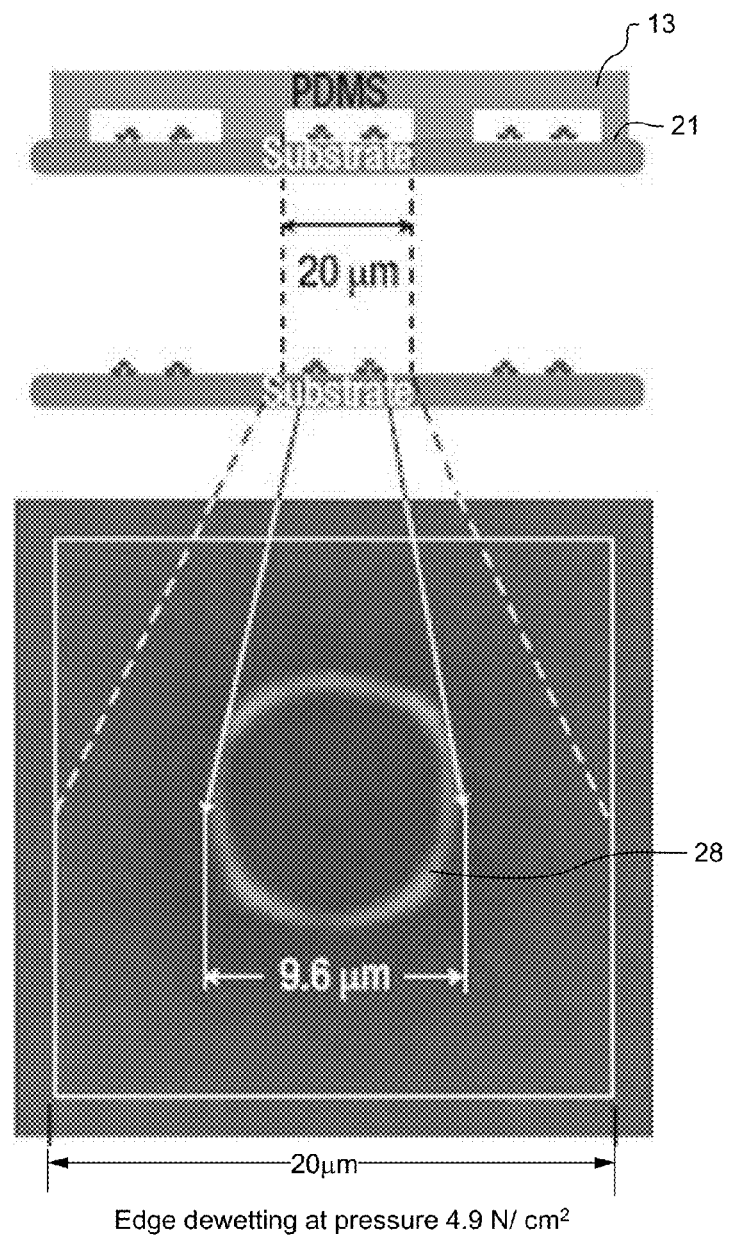
FIG. 4b illustrates a center-defined corral formed through a center-dewetting process (high pressure: 4.9 N/cm$^2$; cell dimension: 20 μm×20 μm sides; 8.5 μm depth)
Figure 4C:
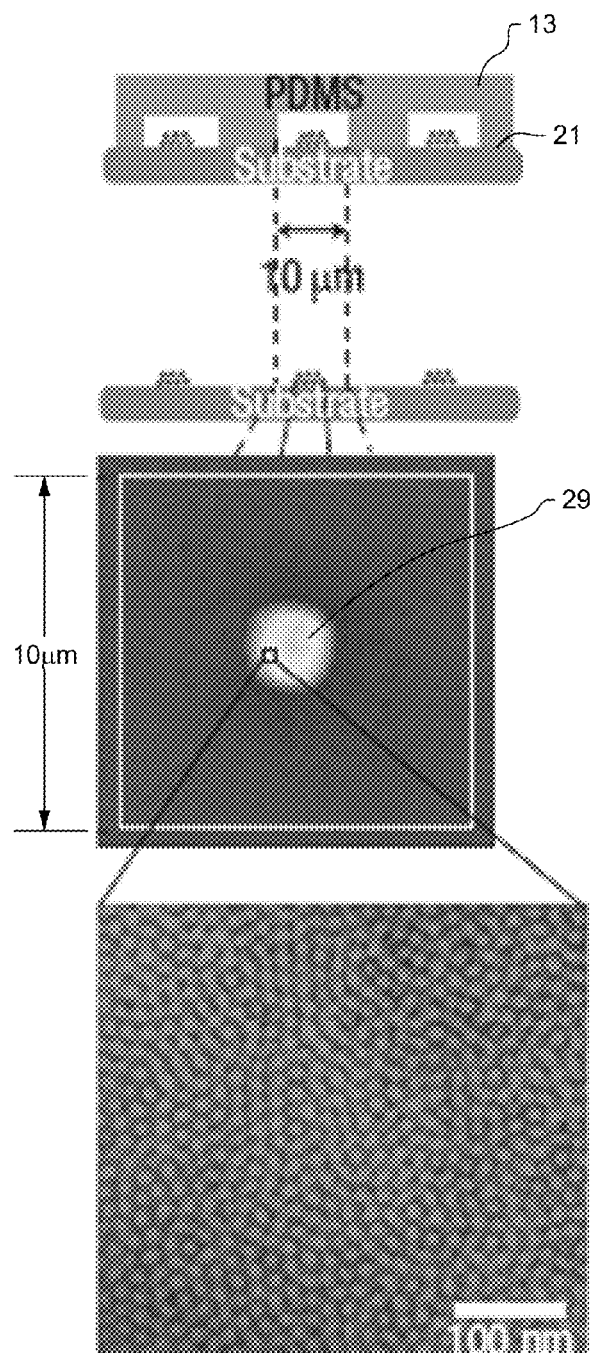
FIG. 4c illustrates a center-defined supra-crystal formed through a center-dewetting process (high pressure: 4.9 N/cm$^2$; cell dimension: 10 μm×10 μm sides; 8.5 μm depth)

Under a high molding pressure, however, only center-dewetting occurs, in which nucleation and growth of superlattices are generally confined to the center of the micro-mold, forming either a shrunken micro-corral 28 (FIG. 4b) or a 3D supra-crystal 29 (FIG. 4c). Notably, the shrunken micro-corral 28 is still square-like, resembling its micro-mold geometry, which indicates that it might evolve from the edge-defined corrals formed at the early-stage dewetting. This particular geometry indicates that the depinning of a microdroplet may depend on its contact line geometry. Specifically, for depinning to occur, the surface tension of a molded microdroplet may need to overcome the force of the resistance nanoparticle deposit, which has a higher value in the corner due to a higher surface-to-volume ratio.

Besides molding pressure, the aspect ratio (depth/diameter) of the micro-mold may also affect the overall morphology of superlattices formed through the disclosed methods and apparatus. As indicated in Table 1 below, edge dewetting is dominant for micro-molds with a low aspect-ratio, whereas center dewetting is dominant for micro-molds with a high-aspect-ratio micro-mold. Hence, both corrals and 'supra-crystals' may be obtained when different

TABLE 1

Effects of aspect ratios of micro-molds on dewetting dynamics

Figure 5:
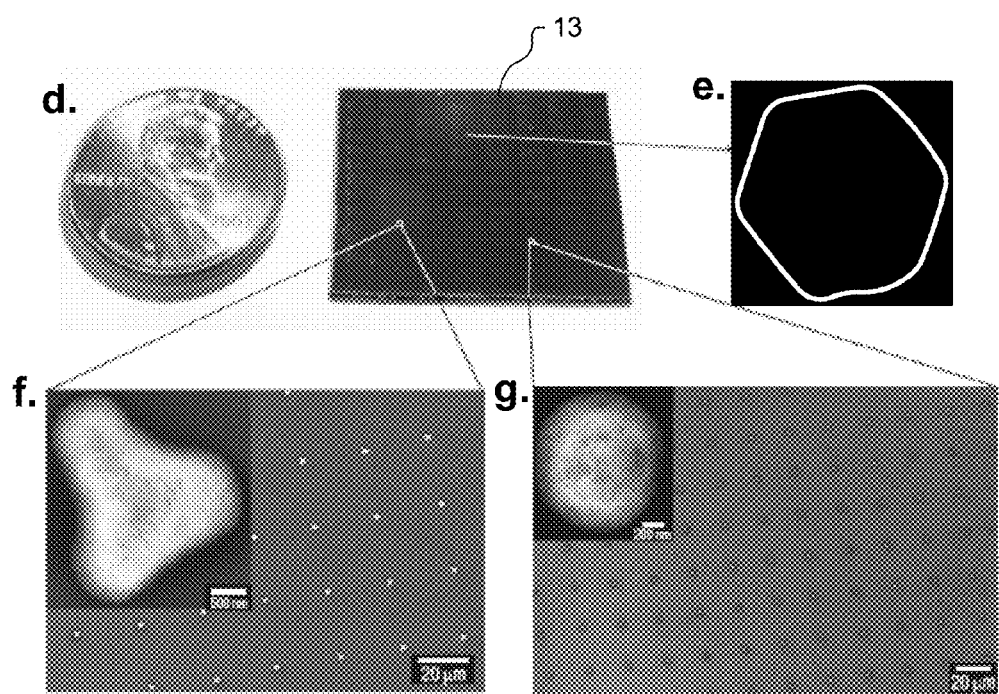
FIG. 5 illustrates the use of a multiplexed micro-mold to form edge-defined corrals and center-defined supra-crystals of various shapes under the same pressure in a single step.

| Aspect ratio (depth/diameter) | Dewetting dynamics |
|---|---|
| 0.05 (1/20) | Edge dewetting |
| 0.1 (1/10) | Edge dewetting |
| 0.25 (5/20) | Edge dewetting |
| 0.425 (8.5/20) | Center dewetting/Edge dewetting |
| 0.85 (8.5/10) | Center dewetting |
| 0.9 (18/20) | Center dewetting | micro- or nano-features are integrated into a multiplexed micro-mold with different lateral dimensions, allowing us to pattern superlattices into various structures on the same silicon substrate in a single step, as illustrated in FIG. 5. Notably, the patterned superlattices may be scaled up to cover a relatively large area. The image of patterned superlattices on a silicon substrate (20×25 mm$^2$) in FIG. 5 indicates that that the multiplexed micro-mold 13 may be used to pattern well-defined self assembly arrays of the substance 15 on different locations of the substrate 11 with relatively unsophisticated means of pressure control (e.g. weights).

Figure 6:
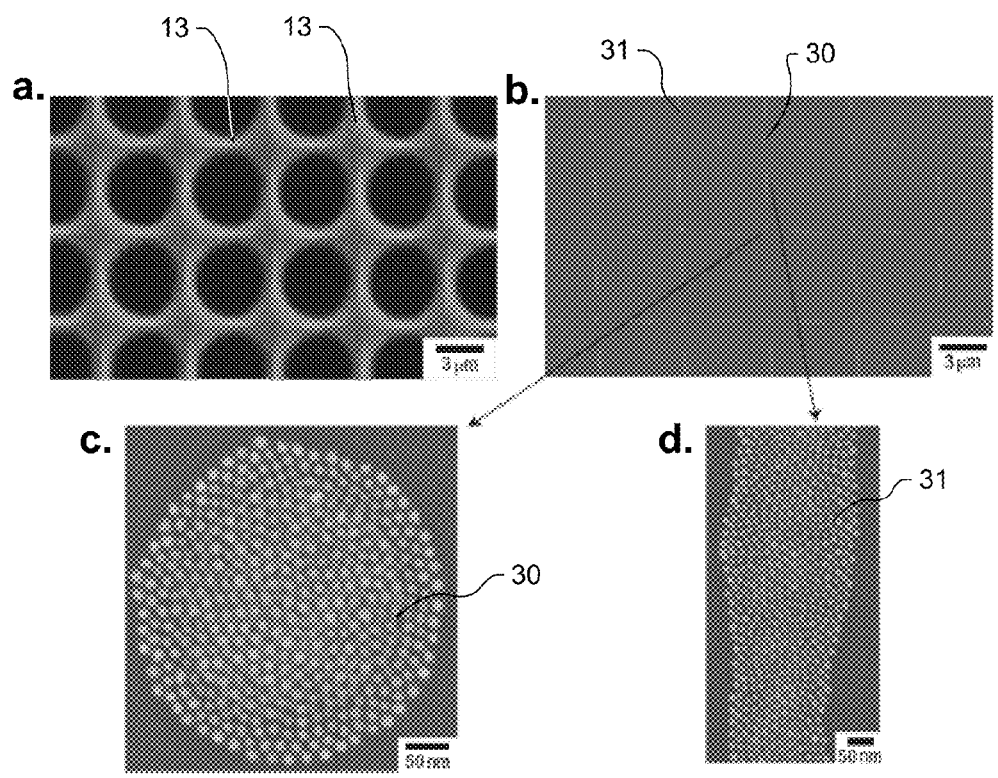
FIG. 6 are SEM images of a close-spaced micro-mold (upper left) and nanoparticle discs and nanoparticle lines formed by using a close-spaced micro-mold.

Another parameter that may affect the dewetting dynamics of the liquid composition and thus the structures of the self-assembled superlattice formed through the disclosed methods and apparatus is the inter-cell spacing and edge geometry of the micro-mold. Specifically, a close-spaced micro-mold may allow the microdroplets in neighboring cells to merge during dewetting. As illustrate in FIG. 6, in an edge dewetting process, microdroplets in neighboring micro-molds may formed dot-like and line-like superlattices corresponding to the protrusions of the bottom edge 21 of the micro-mold 13. As a result, the superlattices may self-assemble into nanoparticle discs 30 and nanoparticle wires 31 with a relatively high degree of internal order.

Figure 7:
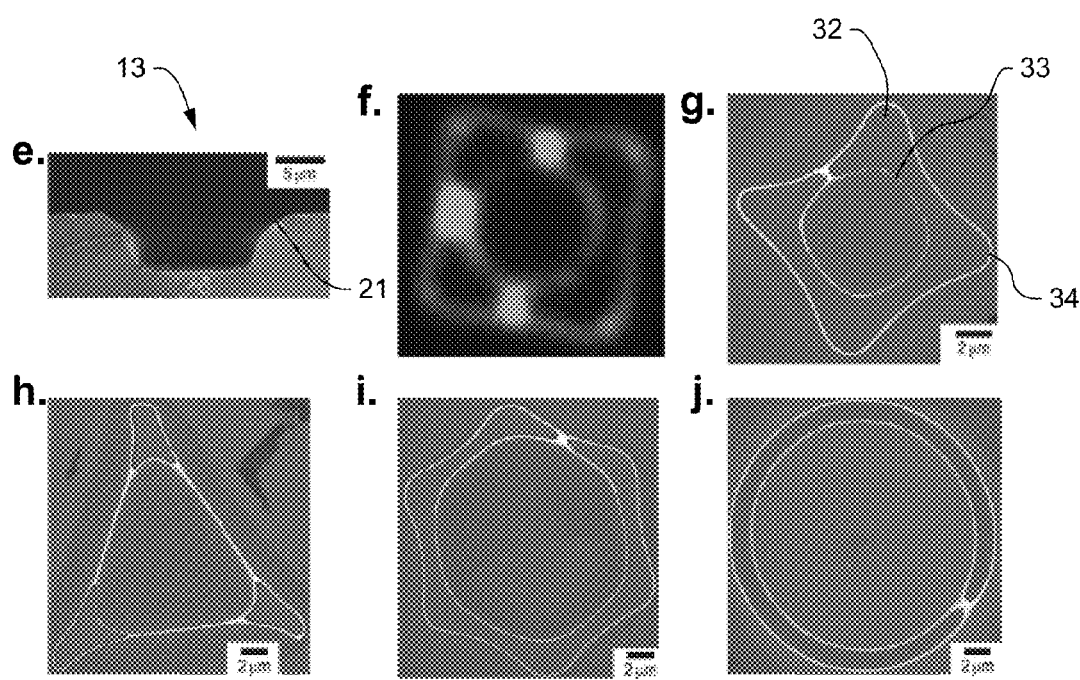
FIG. 7 are SEM images of micro-molds with blunt bottom edges (upper left) and double-corrals of various shapes formed by using a blunt-edge micro-mold of various shapes.

In addition to spacing, edge geometry may also influence local dewetting dynamics. As illustrated in FIG. 7, when the bottom edge 21 of the micro-mold 13 is blunt, larger depinning forces are required for the microdroplets to separate from the micro-mold 13 than sharp-edged micro-molds, such as those shown in FIGS. 4a-c. As a result, edge dewetting is favored and thicker microdroplet-corrals may be formed, resulting in two discrete contact lines: an outer micro-mold edge-defined contact line and an inner contact line governed by surface tension. As the flow of the solvent 16 during dewetting may be directed towards both pinned contact lines, double-corral structures 32 with concentric inner and out micro-corrals (33, 34) may be generated with a relatively high degree of internal order. Still referring to FIG. 7, bridges may be formed between the inner and outer micro-corrals (33, 34) during the final stage of dewetting. Although the bridges show in FIG. 7 are randomly positioned within the double-corral structure 32, their location may be regulated if the spatial distribution of evaporation fluxes and solvent flow can be directionally controlled.

Figure 8:
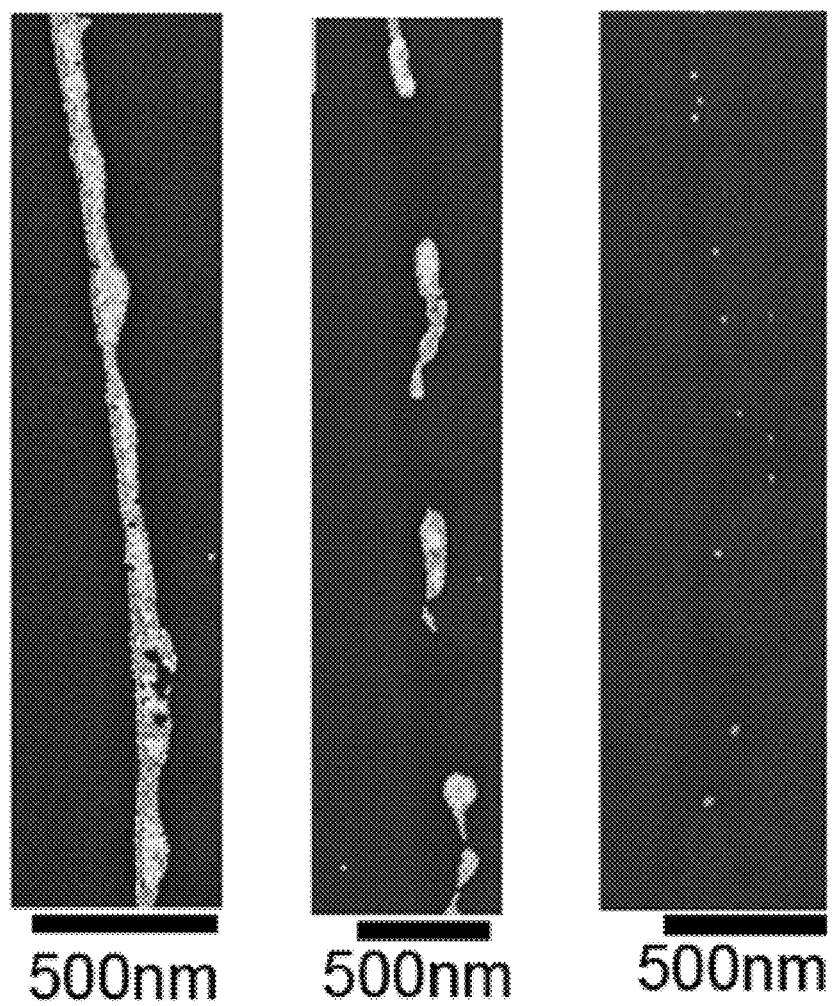
FIG. 8 illustrates the effect of nanoparticle concentrations (from left to right, 1.8 μM; 1.0 μM; 0.16 μM) on edge-defined corrals formed through an edge-dewetting process.
Figure 9:
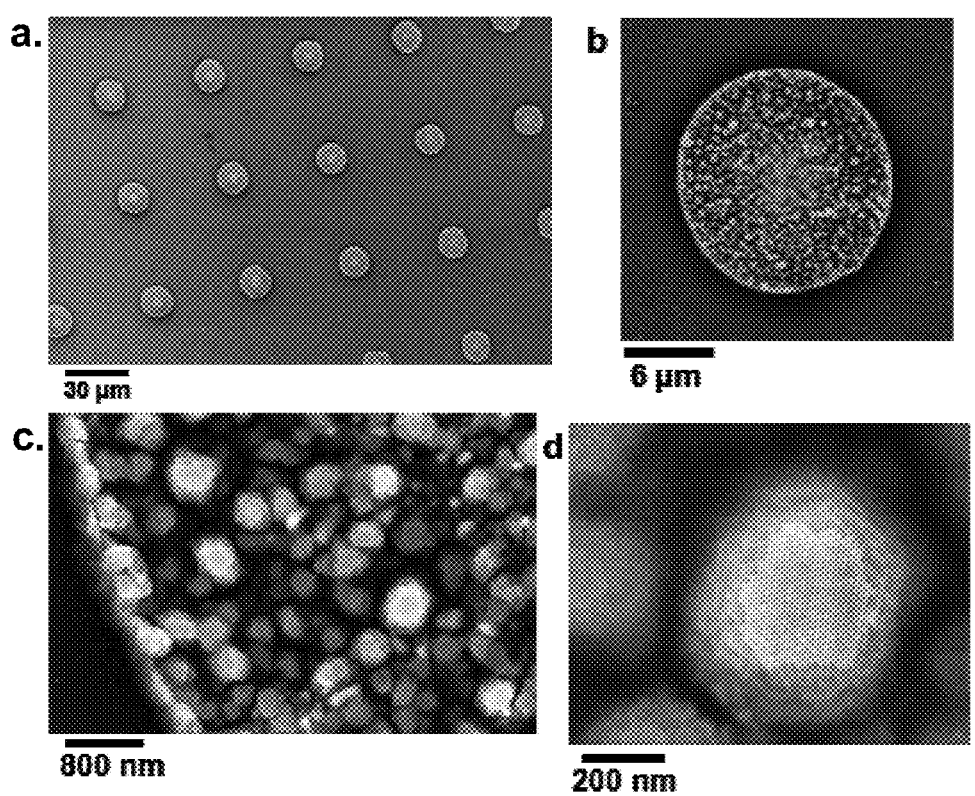
FIG. 9 illustrates SEM images of supra-crystals formed through a center-dewetting process and TEM micrograph of the array of gold nanoparticles. (pressure: 4.9 N/cm$^2$; cell dimension: 20 μm×20 μm sides; 8.5 μm depth; 1.6 μM nanoparticle concentration)

The concentration of the substance 15 may also affect the dewetting process and the structure of the superlattice formed. In edge dewetting processes, as concentrations of the substance 15 increase, nanoparticle corrals may become more continuous with increased heights and widths, as illustrated in FIG. 8. In center dewetting processess, low concentrations of the substance may result in shrunken corrals, whereas high concentrations of the substance may lead to formation of 3D high-quality supra-crystals, as illustrated in FIG. 9.

To maintain a high degree of internal order, the nucleation and growth of superlattices may need to be synchronized with the dewetting dynamics of molded microdroplets. One feature of DNA-capped nanoparticles is that the interparticle potential can be tuned by adjusting the salt concentration within an operation range. Specifically, if the salt concentration is too high, strong electrostatic screening assists rapid DNA hydrogen bonding, which locks nanoparticles together when they come into contact with each other. Such rapid nucleation, under certain conditions, may result in irreversible disordered aggregates, even at a relatively low solubility limit. On the other hand, if the salt concentration is too low, the interactions among nanoparticles may be too repulsive for superlattices to nucleate and grow. As a result, aggregation may not occur until drying is nearly complete, which affords no annealing time for crystallization.

When the salt concentration is within operation range (e.g. 0.1-10 mM NaCl), highly ordered superlattices of DNA-capped nanaoparticles may be formed. It is to be understood that the aforementioned concentration range is simply a non-limiting example and one of ordinary skill in the art could determined the proper operation range according to the DNA-capped nanoparticle, the salt, and the solvent used in the liquid composition without undue experimentation. For sufficiently concentrated liquid compositions, homogeneous nucleation may occur in molded microdroplets, leading to patterned supra-crystals as illustrated in FIG. 9. Otherwise, superlattices may grow heterogeneously on the silicon substrate.

Figure 10:
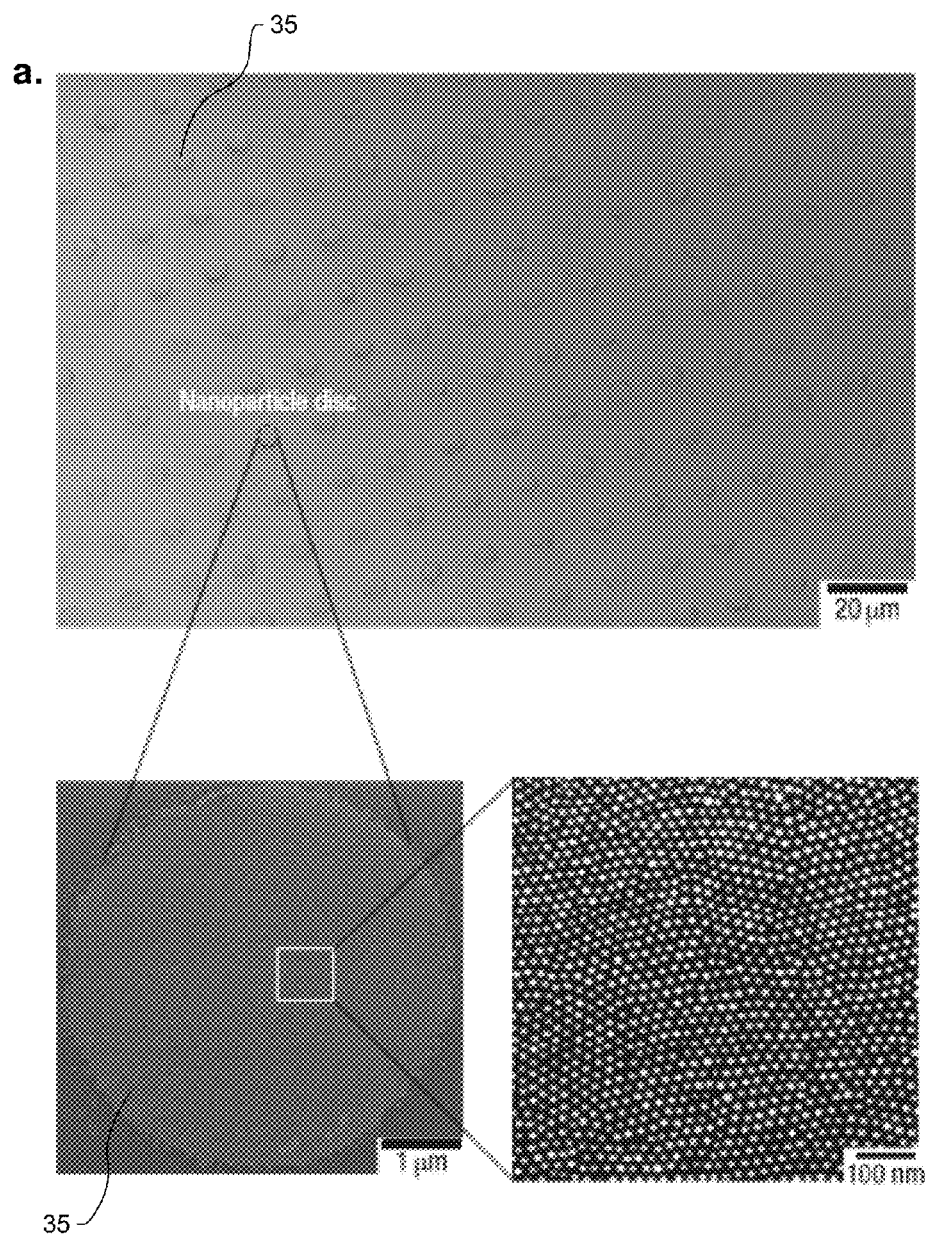
FIG. 10 illustrates a single layer nanoparticle disc formed through synchronized contact line crystallization and center dewetting. (pressure: 3 N/cm$^2$; cell dimension: 5 μm diameter; 3.3 μm depth; 1.0 μM nanoparticle concentration)
Figure 11:
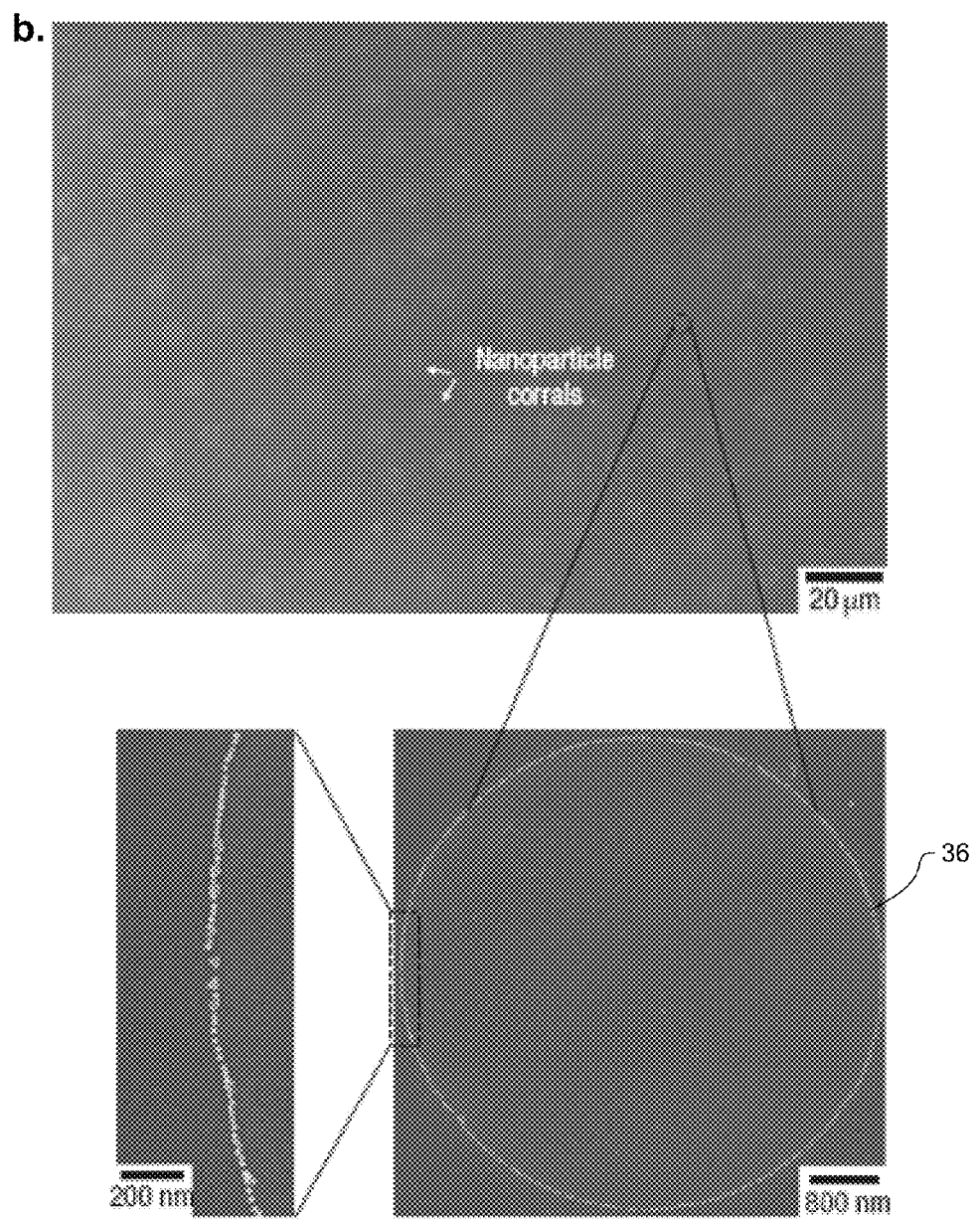
FIG. 11 illustrates a single particle corral formed through synchronized contact line crystallization and edge-dewetting. (pressure: 3 N/cm$^2$; cell dimension: 5 μm diameter; 3.3 μm depth; 330 nM nanoparticle concentration)
Figure 12:
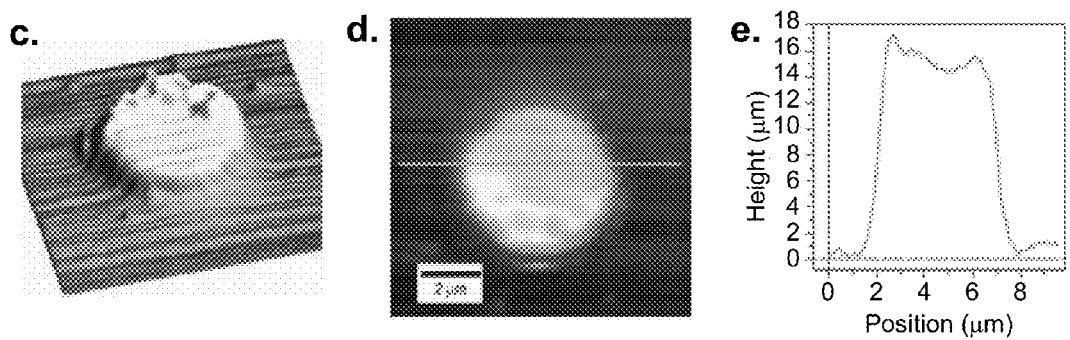
FIG. 12 illustrates AFM characterizations of the nanoparticle disc in FIG. 10 with 3D view (left), 2D view (center), and surface plot (right) of the center line in the 2D view.
Figure 13:
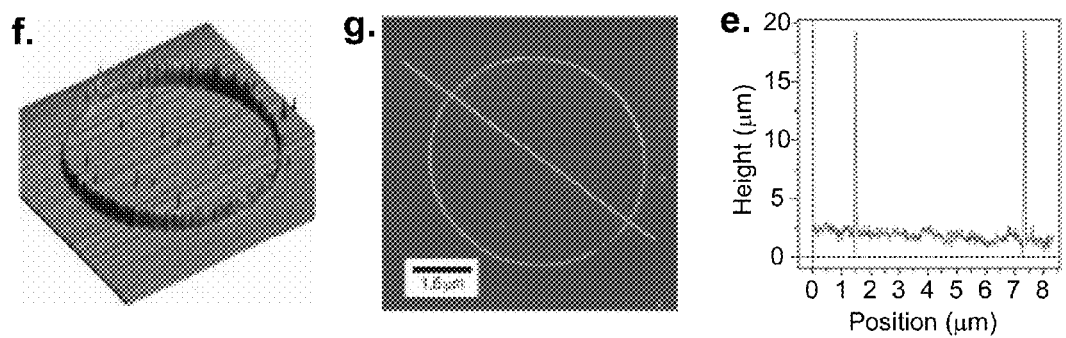
FIG. 13 illustrates AFM characterizations of the single particle corral in FIG. 11 with 3D view (left), 2D view (center), and surface plot (right) of the center line in the 2D view.

When contact line crystallization is synchronized with center dewetting, mono-layered nanoparticle micro-discs 35 may be formed as shown in FIG. 10. When contact line crystallization is synchronized with edge dewetting, on the other hand, micro-corrals 36 may be formed as shown in FIG. 11. The width of nanoparticle micro-corrals 36 may even be reduced to single-particle diameter (e.g. 12 nm) as illustrated in FIGS. 11 and 13, although some defects may exist due to the stochastic nature of drying-mediated self-assembly. Notably, the 12-nm-width micro-corrals 36 may be obtained from a micro-mold with cells dimensioned at about 5 μm diameter, a significant resolution enhancement heretofore unknown. In contrast, stencil-confined printing of 100-nm polystyrene beads or 60-nm nanoparticles known in the art merely translates the resolution from the stencil to the substrate and requires the use of laborious high-resolution lithographic techniques such as electron beam lithography.

As discussed above, self-assembled superlattices may be effectively deposited or patterned on a substrate by molding microdroplets and/or controlling the dewetting dynamics of the liquid composition. It is also contemplated that this combined top-down and bottom-up assembly strategy may also impart desirable properties of superlattices to other nanoscale optical and electronic devices. In one non-limiting embodiment of such devices, electrical interfacing of superlattices may be constructed and addressed by microfabricated electrodes, as demonstrated in greater detail below.

Figure 14:
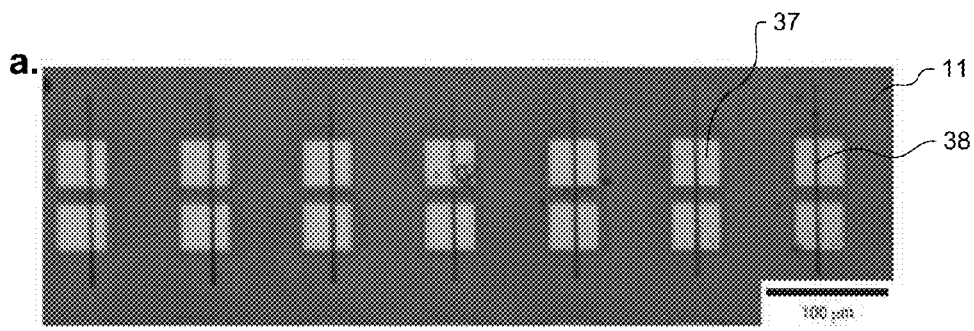
FIG. 14 photographically illustrates mono-layered nanoparticle superlattices formed across microelectrode pairs. (pressure: 2 N/cm$^2$; cell dimension: 5 μm×5 μm sides; 5.3 μm depth)
Figure 15:
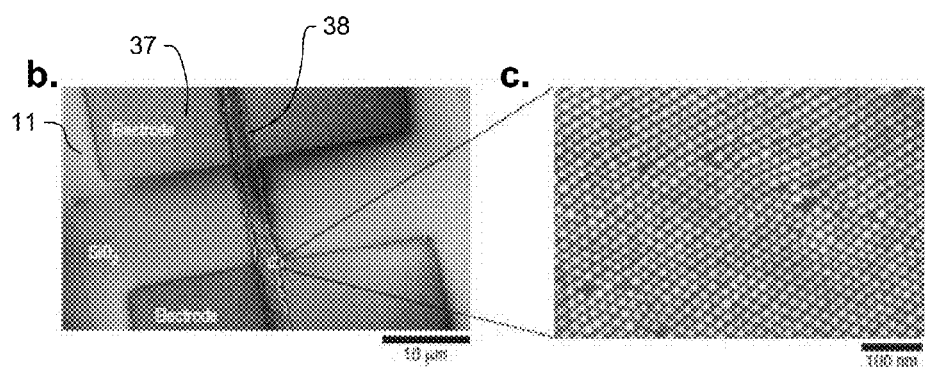
FIG. 15 are SEM micrographs of one nanoparticle superlattice-bridged microelectrode pair in FIG. 14. (pressure: 2 N/cm$^2$; cell dimension: 5 μm×5 μm sides; 5.3 μm depth)

Referring now to FIG. 14, micro-patterned electrode arrays 37 are formed on a silicone plate 38, the combination of which provides the substrate 11 on which nanoparticles may be deposited and patterned. By sandwiching a nanoparticle liquid composition between a PDMS micro-mold and the micro-electrode arrays 37 and the silicon plate 11 (i.e. the substrate 11) with proper alignments, superlattice wires 38 of the nanoparticles may grow directly across pairs of the micro-electrodes 37. Despite the height difference between the micro-electrodes 37 and the silicon plate 38, (e.g. 60 nm), the superlattice wires 38 may be formed with structural continuity and a high degree of internal order, as shown in FIG. 15. The average interparticle spacing was 20.6±1.5 nm, corresponding to an edge-to-edge interparticle spacing of about 8 nm. Unlike close-spaced monolayer-protected-cluster films known in the art, the large gap in the monolayered superlattice structure may prevent electron tunneling from metal core to metal core in the nanoparticles, resulting in insulator-like electronic characteristics.

Figure 16:
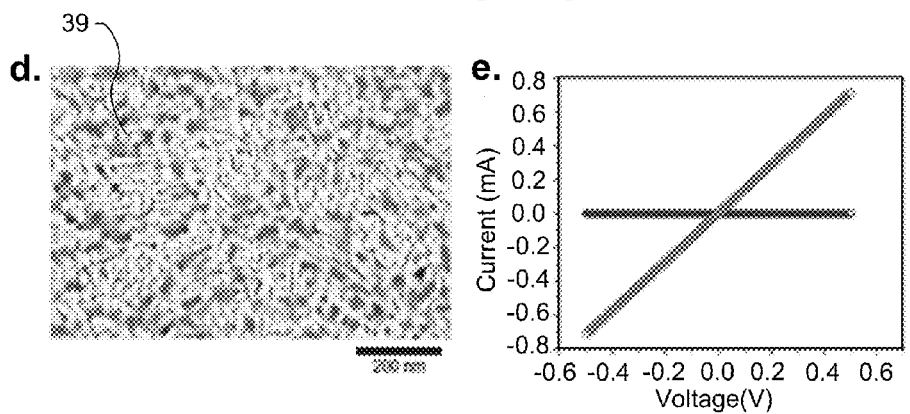
FIG. 16 illustrates the effect of annealing on microstructure (left) and conductivity (right) of the superlattice in FIGS. 14-15.

The electronic properties of such unique superlattice wires 38 can be further modulated by doping DNA-binding ions, dyes or superconductor molecules (such as tetrathiafulvalene) or, more easily, by thermal annealing. For example, the nanoparticles may be fused into a porous metallic film 39 after annealing, which may enhance electronic conductivity, as illustrated in FIG. 16. Specifically, a resistivity of $4.02 \times 10^{-7}$ Ω may be achieve by the annealed gold nanoparticle wires, which is about 16 times the bulk gold resistivity ($2.44 \times 10^{-8}$ Ω). Without wishing to be bound by any particular theory, the high resistivity may be related to the porous nature of the nanoparticle wires. Hence, controlling porosity (for example, by programming the annealing temperature) may allow for further fine-tuning of wire conductivities.

Figure 17:
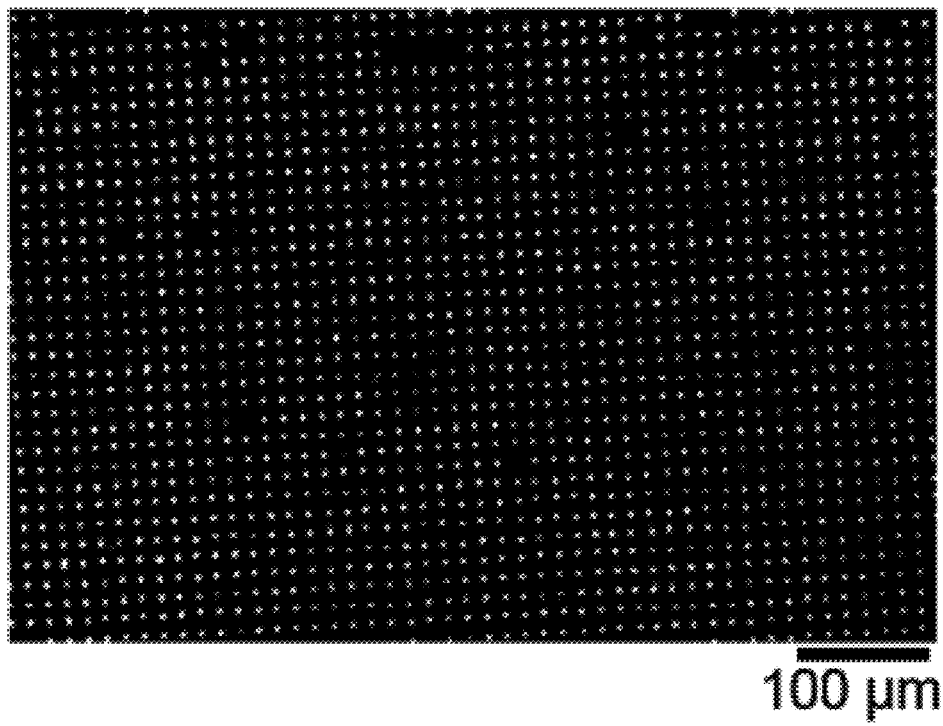
FIG. 17 illustrates the use of the disclosed method and apparatus to deposit and pattern quantum dots on a substrate through a center-dewetting process.)
Figure 18:
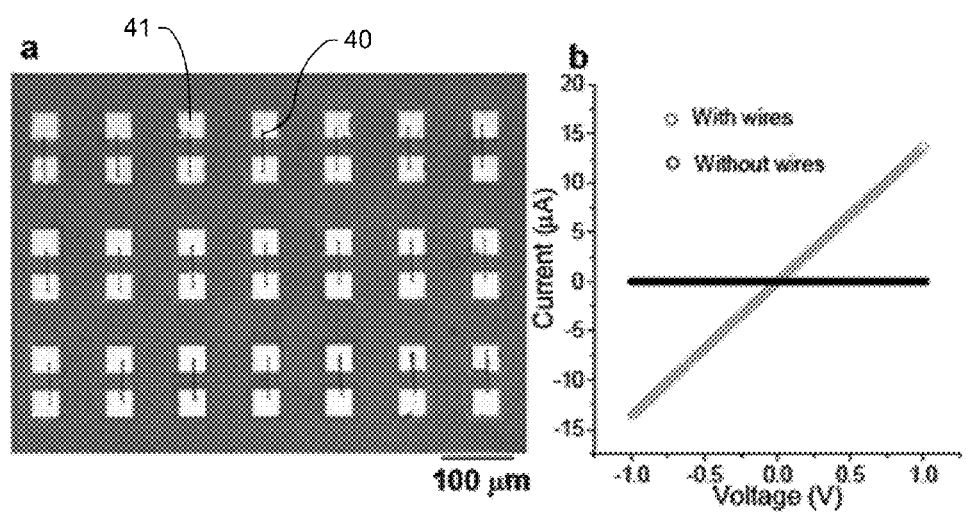
FIG. 18 illustrates the use of the disclosed method and apparatus to form conductive polymer superlattices across microelectrode pairs (left) and the effect of the superlattice bridge on the conductivity of the microelectrodes (right). (pressure: 2 N/cm$^2$; cell dimension: 5 μm×5 μm sides; 5.3 μm depth)

In addition to transition metal nanoparticles, the molded microdroplet approach disclosed herein may also be generalized to regulate the drying-mediated deposition of a variety of materials. As illustrated in FIG. 17, CdSe/ZnS quantum dots may be patterned on a substrate with high orders of regularity. Moreover, conducting polymers in dilute suspensions may also be molded and dewetted according to this disclosure. As shown in FIG. 18, micro-wires 40 of poly(3,4-ethylenedioxythiophene)-poly(styrenesulfonate) may be formed across micro-electrode pairs 41. A resistivity of $8.24 \times 10^{-3}$ Ω may be achieve by the conductive polymer wires 40, which is consistent with the bulk resistivity of the conductive polymer ($9.0 \times 10^{-3}$ Ω), indicating that electronic properties of the conductive polymers are not adversely affected by the disclosed methods and apparatus.

Figure 19:
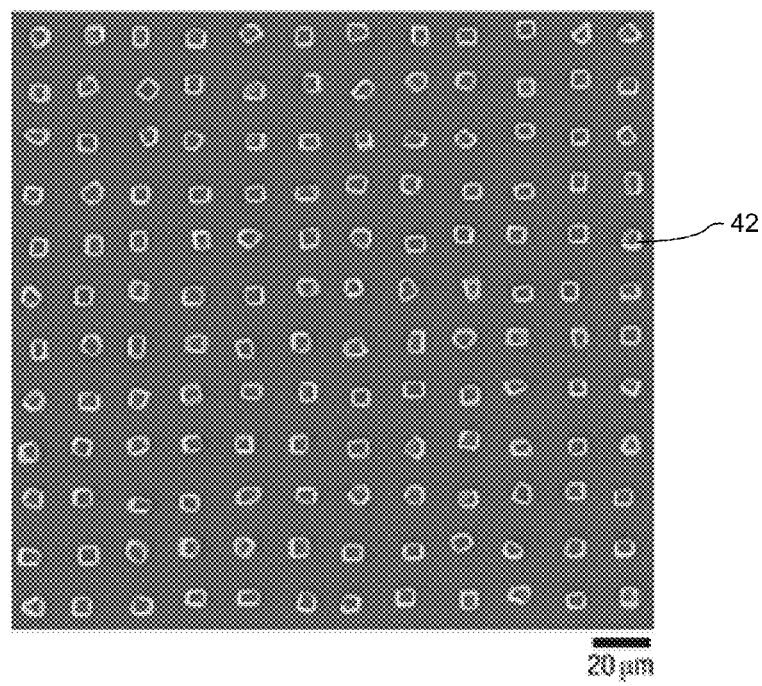
FIG. 19 illustrates the use of the disclosed method and apparatus to deposit and pattern single crystals of a crystalline salt on a substrate through a center-dewetting process using a square micro-mold (pressure: 3.1 N/cm$^2$; cell dimension: 10 μm×10 μm sides; 7.6 μm depth; 2M salt concentration)
Figure 19:
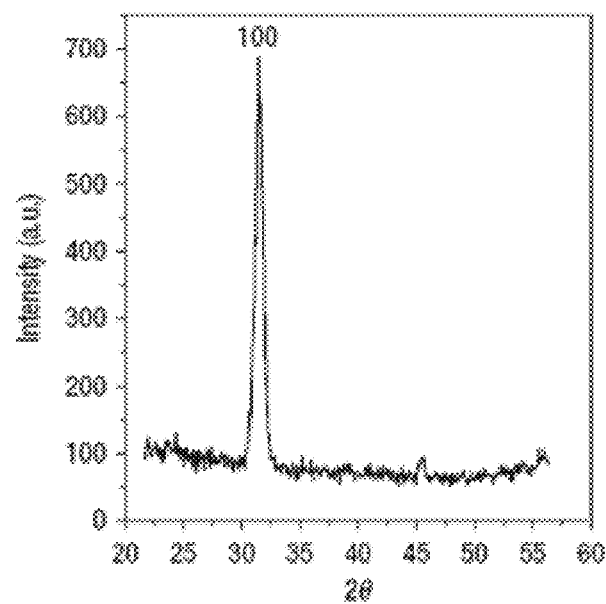
Figure 20:
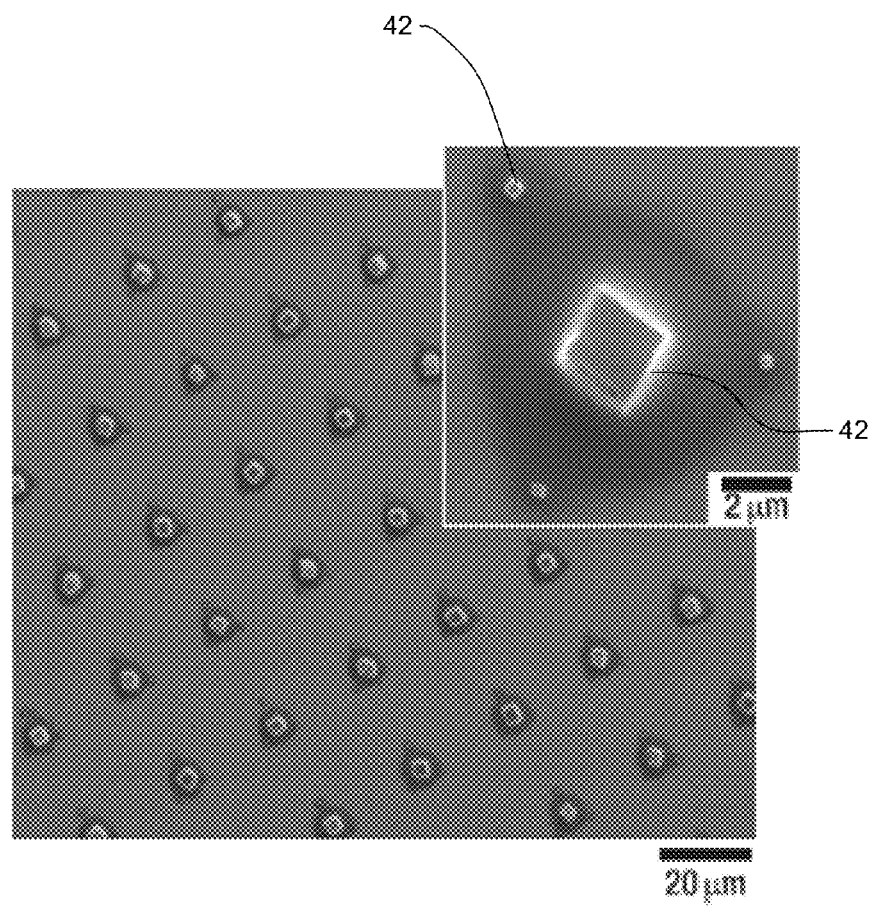
FIG. 20 illustrates the use of the disclosed method and apparatus to deposit and pattern single crystals of a crystalline salt on a substrate through a center-dewetting process using a triangular micro-mold (pressure: 1.4 N/cm$^2$; cell dimension: 20 μm sides; 8.5 μm depth; 1M salt concentration)

Finally, the molded microdroplet approach disclosed herein may be further extended to pattern single-crystal arrays. In particular, crystal size, nucleating location, density and crystallographic orientation may be controlled through PDMS mold design and local dewetting regulation. For example, SEM micrographs of patterned NaCl single-crystal arrays clearly show that crystal size and location may be controlled with relatively high precision (FIGS. 19-20). Moreover, the orientations may also be controlled by micromold geometry. In particular, cubic NaCl crystals 42 may grow with their facets parallel to the sides of square micro-molds owing to spatial confinement, as illustrated in FIG. 19. X-ray characterization also confirmed that the top planes of these crystals are always (100) facets. For triangular micro-molds, however, cubic NaCl 42 crystals did not match their corresponding mold geometries and therefore four nucleating events may occur at the center and three corners of each micro-mold, as illustrated in FIG. 20. Without wishing to be bound by any particular theory, it is contemplated that the corner nucleation is perhaps due to a longer retention time of the microdroplet at the corners, resulting from insufficient depinning forces. Notably, localized crystallization events may be controlled in a single step with a high placement accuracy without any surface chemical treatment, unlike known single-crystal patterning methods in which surface modification is required.

Exemplary Methods and Materials

Fabrication of PDMS Micro-Molds

PDMS molds were fabricated by molding from a SU-8 master or reactive ion etching (RIE), depending on the specific requirements. The conventional PDMS molds were prepared as follows. First, the SU-8 master was generated by standard photolithography followed by surface modification with trichloro(3,3,3-trifluoropropyl)silane. A mixture of base and curing agent (10:1 w/w) of Sylgard 184 silicone elastomer was then poured onto the patterned SU-8 surface and cured at 75° C. for 3 h. The PDMS molds were obtained by peeling off from the SU-8 master.

To fabricate close-spaced or blunt-edged PDMS molds, RIE was combined with photolithography. PDMS was first spin-coated onto $O_2$-plasma-treated silicon wafers to a thickness of about 50 μm, followed by a layer of SPR 220-4.5 spin-coated to a thickness of 3-8 μm. In order to improve the adhesion, PDMS was treated with $O_2$ plasma before spin-coating the photoresist. After exposure and development, the patterned substrate was then dry etched using a 1:3 ratio of $O_2$:$CF_4$. The etch time may be varied with shorter etch times resulting in shallow micro-molds with sharp edges, and longer etch times resulting in deep micro-molds with smoothly curved (blunt) edges. For PDMS micro-molds with close-packed features (FIG. 6), long etch times resulted in overlapping of neighboring micro-molds.

Molding Microdroplets and Pattern Formation

Both the substrate and the PDMS micro-mold were sonicated for 3 min in ethanol and dried before use. A droplet of aqueous composition containing the substance (nanoparticles, quantum dots, conducting polymers, crystalline salts, fluorescent dyes, etc), was sandwiched between the PDMS micro-mold and the solid substrate. A weight was placed on top of the PDMS mold to control the molding pressure. After complete drying of the microdroplets, the PDMS micro-mold was peeled off, leaving the substance deposits on the solid substrates.

Synthesis of DNA-Capped Gold Nanoparticles

Gold nanoparticles with a diameter of about 12 nm were synthesized according to known literature procedures. ssDNA capped nanoparticles were also synthesized according to known literature procedures, with some modifications. In an exemplary preparation, 5'-thiolated oligonucleotides (Integrated DNA Technologies) were deprotected and incubated with nanoparticle solutions at a 1000:1 ratio of DNA to nanoparticle for 12 h at room temperature. Sodium chloride was then added to a final concentration of 0.2 M. The mixture was aged at room temperature for another 10-12 h and was then centrifuged at 14,500 r.p.m. and the supernatant was exchanged with Milli-Q water.

Instrumentation

Transmission electron microscopy (TEM) images were acquired using a Tecnai T12 (FEI) operating at an acceleration voltage of 120 kV. Atomic force microscopy (AFM) measurements were carried out on a Dimension 3100 scanning probe microscope (Veeco Instruments) in tapping mode using a silicon cantilever. SEM images were obtained using a field-emission scanning electron microscope (ZEISS, LEO 1550) with an operating voltage of 2-5 kV. Microdroplets containing AlexaFluor 488 were imaged using a fluorescent microscope (Olympus, 1×71). Conductivities were measured using the Agilent 4156C Precision Semiconductor Parameter Analyzer.

While only certain embodiments have been set forth, alternative embodiments and various modifications will be apparent from the above descriptions to those skilled in the art. These and other alternatives are considered equivalents and within the spirit and scope of this disclosure.

What is claimed is:

1. An apparatus for forming self-assembly arrays of nanoparticles or quantum dots, the apparatus comprising:
    a substrate supporting a liquid composition including a plurality of a substance and a solvent, the solvent being an aqueous solution, the substance being selected from a group consisting of a nanoparticle and a quantum dot, the nanoparticle or the quantum dot comprising a center core and spacer ligands attached to the center core, the center core including a transition metal and the spacer ligands consisting of nucleic acids; and
    a removable micro-mold placed over the substrate and the liquid composition, the solvent being evaporated through at least one evaporation channel formed between the micro-mold and the substrate, the evaporation of the solvent through the at least one evaporation channel mediating a self-assembly of the plurality of the substances into an array deposited on the substrate, the array being internally organized into a superlattice.

2. The apparatus of claim 1, wherein the evaporation channel is adjustable by subjecting the micro-mold to a positive pressure.

3. The apparatus of claim 2, wherein the evaporation of the solvent through the at least one evaporation channel further mediates a patterning of the superlattice into at least one defined morphological structure deposited on the substrate.

4. The apparatus of claim 1, wherein the micro-mold is made of polydimethylsiloxane.

5. The apparatus of claim 1, wherein the micro-mold comprises at least one cell defined by a continuous sidewall, the evaporation channel being formed between the substrate and the sidewall.

6. An apparatus for bridging microelectrodes with self-assembly arrays of nanoparticles or quantum dots, the apparatus comprising:
    a substrate with at least two microelectrodes deposited on the substrate, the substrate supporting a liquid composition including a plurality of a substance and a solvent, the substance being selected from a group consisting of a nanoparticle and a quantum dot, the nanoparticle or the quantum dot comprising a center core and spacer ligands attached to the center core, the spacer ligands consisting of nucleic acids; and
    a removable micro-mold placed over the substrate and the liquid composition and bridging the at least two microelectrodes, the solvent being evaporated through at least one evaporation channel formed between the micro-mold and the substrate, the evaporation of the solvent through the at least one evaporation channel mediating a self-assembly of the plurality of the substances into an array, the array forming a bridge across the at least two microelectrodes and being internally organized into a superlattice.

7. The apparatus of claim 6, wherein the evaporation of the solvent through the at least one evaporation channel further mediates a patterning of the superlattice into at least one defined morphological structure deposited on the substrate.

8. The apparatus of claim 7, wherein the at least one defined morphological structure is a superlattice wire that bridges the at least two microelectrodes.

9. A method for forming self-assembly arrays of nanoparticles or quantum dots on a substrate, the method comprising:
    depositing on the substrate a liquid composition including a plurality of a substance and a solvent, the substance being selected from a group consisting of a nanoparticle and a quantum dot, the nanoparticle or the quantum dot comprising a center core and spacer ligands attached to the center core, the spacer ligands consisting of nucleic acids;
    placing a removable micro-mold over the substrate and the liquid composition;
    allowing the solvent to be evaporated through at least one evaporation channel formed between the micro-mold and the substrate; and
    allowing the plurality of the substance to self-assemble into an array deposited on the substrate during the evaporation of the solvent through the at least one evaporation channel, the array being internally organized into a superlattice.

10. The method of claim 9, further comprising applying positive pressure to the micro-mold when the solvent is evaporated through the evaporation channel.

11. The method of claim 10, further comprising allowing the superlattice to form at least one defined morphological structure during the evaporation of the solvent through the at least one evaporation channel.

12. The method of claim 11, wherein the at least one defined morphological structure comprises a structure selected from a group consisting of an edge-defined corral, a center-defined corral, a supra-crystal, a double corral, a disc, a wire, and combinations thereof.

13. The method of claim 9, wherein the micro-mold is made of polydimethylsiloxane.

14. The method of claim 9, wherein the center core is a transition metal.

15. The method of claim 9, wherein the micro-mold comprises at least one cell defined by a continuous sidewall, the evaporation channel being formed between the substrate and the sidewall.

16. A method for forming self-assembly arrays of nanoparticles or quantum dots that bridge at least two microelectrodes on a substrate, the method comprising:
    depositing on the substrate a liquid composition including a plurality of a substance and a solvent, the substance being selected from a group consisting of a nanoparticle and a quantum dot, the nanoparticle or the quantum dot comprising a center core and spacer ligands attached to the center core, the spacer ligands consisting of nucleic acids;
    placing a removable micro-mold over the substrate and the liquid composition, the micro-mold bridging the at least two microelectrodes;
    allowing the solvent to be evaporated through at least one evaporation channel formed between the micro-mold and the substrate; and
    allowing the plurality of the substance to self-assemble into an array forming a bridge across the at least two microelectrodes during the evaporation of the solvent through the at least one evaporation channel, the array being internally organized into a superlattice.

17. The method of claim 16, further comprising applying positive pressure to the micro-mold when the solvent is evaporated through the evaporation channel.

18. The method of claim 16, further comprising allowing the superlattice to form at least one defined morphological structure during the evaporation of the solvent through the at least one evaporation channel.

19. The method of claim 18, wherein the at least one defined morphological structure is a superlattice wire that bridges the at least two microelectrodes.

\* \* \* \* \*